US00PP27186P2

(12) United States Plant Patent
Kordes

(10) Patent No.: US PP27,186 P2
(45) Date of Patent: Sep. 27, 2016

(54) MINIATURE ROSE PLANT NAMED 'KORPOT045'

(50) Latin Name: *Rosa hybrida*
Varietal Denomination: KORpot045

(71) Applicant: Tim Hermann Kordes, Klein Offenseth-Sparrieshoop (DE)

(72) Inventor: Tim Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 99 days.

(21) Appl. No.: 14/544,451

(22) Filed: Jan. 7, 2015

Related U.S. Application Data

(60) Provisional application No. 61/965,477, filed on Jan. 31, 2014.

(51) Int. Cl.
*A01H 5/02* (2006.01)

(52) U.S. Cl.
USPC ..... Plt./118

(58) Field of Classification Search
USPC ..... Plt./116, 118
See application file for complete search history.

*Primary Examiner* — Susan McCormick Ewoldt

(57) ABSTRACT

A new and distinct variety of rose with long lasting, novel yellow flowers, and attractive foliage with very good disease resistance. It exhibits compact bushy to upright growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORpot045'.

BACKGROUND OF THE INVENTION

The new variety of rose plant of the present invention originated from a controlled crossing in a breeding program of two distinct parents during the summer of 2010. The crossing was between an un-named seedling, the seed parent, and another un-named seedling, the pollen parent by the same inventor.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORpot045'.

SUMMARY OF THE INVENTION

The new rose plant may be distinguished from its seed parent, an un-named seedling, by the following combination of characteristics:

1. 'KORpot045' has yellow flowers, whereas the un-named seedling has apricot colored flowers.
2. 'KORpot045' has a double petal count, whereas the un-named seedling has a semi-double petal count.

The new rose plant may be distinguished from its pollen parent, an un-named seedling, by the following combination of characteristics:

1. 'KORpot045' has yellow flowers, whereas the un-named seedling has orange flowers.

2. 'KORpot045' has a moderately bushy plant habit, whereas the un-named seedling has a taller and more upright plant habit.

The objective of the hybridization was to create a new and distinct rose plant with unique qualities, such as:

1. Compact and uniform growth and flowering under greenhouse conditions when grown as a potted floral plant;
2. Abundant, long lasting, and attractive flowers and foliage;
3. Resistance to diseases encountered in greenhouse and nursery culture; and
4. Suitability for production from softwood cuttings in floral and nursery containers.

This combination of qualities is not present in prior rose cultivars known to the inventor. These objectives have been substantially achieved and in that distinguish 'KORpot045' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORpot045' was selected in April, 2011 from the seedling beds to be asexually propagated for further evaluation. The first asexual propagation of 'KORpot045' was done by rooting softwood cuttings in June 2011 at the inventor's nursery in Offenseth-Sparrieshoop, Germany.

These initial and other subsequent propagations conducted in controlled environments demonstrate that 'KORpot045' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORpot045'.

DETAILED BOTANICAL DESCRIPTION

The following is a description of 'KORpot045', as observed growing in November, 2014 in a nursery in Jackson County, Oreg. on plants of 6 months of age. Color references are made using The Royal Horticultural Society (London, England) Colour Chart, 2001 except where common terms of color are used.

For a comparison, several physical characteristics of the rose variety 'KORspunty', a rose variety from the same inventor described and illustrated in U.S. Plant Pat. No. 17,402 and issued on Feb. 6, 2007 are compared to 'KORpot045' in Chart 1.

CHART 1

| Characteristic | 'KORpot045' | 'KORspunty' |
|---|---|---|
| Peduncle surface. | Glabrous. No fine hairs or stiptiate glands present. | Smooth with a limited number of fine white hairs. |
| Average open flower diameter. | 55 mm. | 35 mm. |
| Petal count. | Double. Approximately 35 petals under normal conditions. | Very double. Approximately 50 to 60 petals under normal conditions. |

Parents:

*Seed parent.*—An un-named seedling.

*Pollen parent.*—An un-named seedling.

Classification:

*Botanical classification.*—*Rosa hybrida* 'KORpot045'.

*Commercial classification.*—Miniature rose.

FLOWER AND FLOWER BUD

Blooming habit: Recurrent. Floriferous.

Flower bud:

*Size.*—Upon opening, 20 to 25 mm in length from base of receptacle to distal end of bud and 15 to 20 mm diameter at its widest point.

*Bud form.*—Short. Globular.

*Bud color.*—As sepals first unfold, bud color is Green-Yellow Group 1C When ¼ open, the upper surface of petals is Yellow Group 13B, and the lower surface is Yellow Group 13A. Outermost petals are Yellow Group 3A with intonations of Yellow-Green Group 145B along the midrib and in the marginal zone.

*Sepals.*—Color: Upper surface Yellow-Green Group 146B. Lower surface Yellow-Green Group 144A. Intonations of Greyed-Red Group 180A present on apices. Size: Average 25 to 35 mm (l)×5 to 6 mm (w). Shape: Weak foliaceous appendages on three of the five sepals. Apex: Cirrose on those sepal where foliaceous appendages are present, and apiculate on those sepals where foliaceous appendages are absent. Base: Flat at union with receptacle. Quantity: Five. Surface texture: Upper side: Smooth, hoary. Lower surface: Glabrous. Margins: Cilliate. Stipitate glands: Limited numbers present on margins.

Flower bloom:

*Fragrance.*—Light.

*Duration.*—On the plant 18 to 20 days. Senesced petals drop away cleanly.

*Size.*—Large for a miniature rose. When open, the average flower diameter is 55 mm and the average flower height is 30 mm.

*Form.*—Shape: High centered. Shape of flower when viewed from the side: Upon opening, upper part: Flat. Upon opening, lower part: Flattened convex. Open flower, upper part: Flattened convex. Open flower, lower part: Flat.

Color:

*Upon opening, petals.*—Outermost petals: Outer Side: Yellow Group 12B. Inner Side: Yellow Group 12A. Innermost petals: Outer Side: Yellow-Orange Group 14A. Inner Side: Yellow-Orange Group 14B. No distinctive coloration at petal base observed.

*After opening, petals.*—Outermost petals: Outer Side: Yellow Group 12B. Inner Side: Yellow Group 12A. Innermost petals: Outer Side: Yellow Group 13B. Inner Side: Yellow Group 12A. No distinctive coloration at petal base observed.

General tonality: On open flower Yellow Group 13B. No change in the general tonality at the end of the 8th day. Afterwards, general tonality is 13D.

Petals:

*Petal count.*—Double. Approximately 35 petals under normal conditions.

*Petal reflex.*—Petals reflex slightly. Reflex occurs one by one, beginning with outermost petals.

*Petal margin.*—Entire margins observed on outermost petals. Undulated, emarginate margins observed on innermost petals.

*Petal shape.*—Outermost petals: Orbicular. Apex: Obtuse. Base: Obtuse. Innermost petals: Obcordate. Apex: Emarginate. Base: Cuneate.

*Petal size.*—20 to 25 mm (l)×20 to 30 mm (w).

*Petal arrangement.*—Formal.

*Texture.*—Outermost Petals: Inner Side: Smooth. Outer Side: Smooth. Innermost Petals: Inner Side: Wrinkled. Outer Side: Wrinkled.

Petaloids:

*Petaloid count.*—Average of 15 per flower.

*Petaloid size.*—8 to 18 mm (l)×6 to 15 mm (w).

*Petaloid color.*—Inner side: Yellow Group 13A. Outer side: Yellow-Orange Group 14A.

*Petaloid texture.*—Inner Side: Wrinkled. Outer Side: Wrinkled.

*Margins.*—Undulated, emarginate.

*Petaloid shape.*—Most commonly obcordate, with some petaloids highly irregular. Apex: Emarginate. Base: Cuneate.

Reproductive organs:

*Pistils.*—Average. Approximately 60 present. Stigmas: Location: Slightly superior in position to anthers. Color: Greyed-Yellow Group 160A. Styles: Length: About 10 mm long. Color: Greyed-Yellow Group 160D, with intonations of Red Group 50B.

*Stamens.*—Approximately 100 on average and regularly arranged. Anthers: Size: Average 2 to 3 mm (l)×1 to 1.5 mm (w). Pollen: Generally present. Color: Yellow-Orange Group 16A. Filaments: Color: Yellow-Orange Group 14A. Length: 5 mm.

Receptacle:

*Surface.*—Lacking fine hairs and stipitate glands.

*Color.*—Yellow-Green Group 146B.

*Shape.*—Funnel-shaped.

*Texture.*—Glabrous.

*Size.*—5 mm (h)×5 mm (w).

Pedicel: Not present. Flowers borne singularly.

Peduncle:

*Surface*.—Lacking fine hairs and stipitate glands.

*Length*.—70 to 90 mm average length.

*Diameter*.—2 to 4 mm average diameter.

*Color*.—Yellow-Green Group 146A.

*Strength*.—Strong.

*Borne*.—Singularly. Below initiation of inflorescence, flowering laterals are absent.

THE PLANT

Growth: Moderately vigorous.

Plant habit: Compact and upright to bushy. When grown as a 10.5 cm pot plant, the average plant height is 30 cm and the average plant width is 20 cm.

Stems:

*Stem color*.—Young wood: Yellow-Green Group 146C. Older wood: Yellow-Green Group 146A.

*Intonations*.—Greyed-Purple Group 183B, present primarily on young wood.

*Stem surface texture*.—Young wood: Smooth. Older wood: Smooth.

*Length*.—185 mm average length when grown under commercial greenhouse floral production.

*Diameter*.—3 to 3 mm average diameter.

Prickles: Present.

*Incidence*.—Average of 6 per each 10 cm of stem.

*Size*.—Average length: 5 mm.

*Color*.—Immature prickles: Not observed. Mature prickles: Greyed-Red Group 180D.

*Shape*.—Linear.

Leaves: Normally 5 leaflets on normal leaves in middle of the stem.

*Venation pattern*.—Pyramidal net pattern.

*Leaf size*.—100 to 115 mm (l)×55 to 70 mm (w).

*Abundance*.—Moderately abundant.

Leaflets:

*Size*.—Average size of the terminal leaflet is 40 to 45 mm (l)×30 to 35 mm (w).

*Shape*.—Obtuse. Base: Obtuse. Apex: Acute.

*Margins*.—Finely serrated.

*Surface*.—Semi-glossy.

*Texture*.—Upper side of leaflet: Smooth. Under side of leaflet: Rugose.

*Color, mature foliage*.—Upper Leaflet Surface: Green Group 139A. Lower Leaflet Surface: Yellow-Green Group 147B.

*Color, juvenile foliage*.—Upper Leaflet Surface: Yellow-Green Group 146B. Lower Leaflet Surface: Yellow-Green Group 146C.

*Anthocyanin intonation*.—Greyed-Red 178A. Location: Margins, midribs and underside of foliage, most prominent on juvenile foliage.

*Arrangement*.—Odd pinnate.

*Venation*.—Reticulate.

Stipules:

*Size*.—10 mm (l)×4 mm (w).

*Stipule color*.—Yellow-Green Group 146C.

*Anthocyanin*.—Greyed-Red Group 180C, present on margins and base.

*Stipitate glands*.—Limited numbers present on margins.

*Margins*.—Glandular toothed.

*Texture*.—Upper Surface: Smooth with limited numbers of fine hairs present. Underneath: Glabrous.

*Shape*.—Apex: Apiculate. Base: Winged.

Petiole:

*Length*.—Average 20 mm.

*Diameter*.—Average 1 mm.

*Petiole color*.—Yellow-Green Group 146B. Underneath: Yellow-Green Group 146C.

*Margins*.—Entire, with limited numbers of stipitate glands.

*Anthocyanin*.—Greyed-Purple 183B on margins and underneath.

*Prickles*.—Not observed.

*Stipitate glands*.—Limited numbers of stipitate glands present on margins and underneath.

*Texture*.—Upper Surface: Smooth with limited numbers of fine hairs present. Underneath: Glabrous.

Petiole rachis:

*Length*.—Average 20 to 25 mm.

*Diameter*.—Average 1 mm.

*Color*.—Upper Surface: Yellow-Green Group 146A. Underneath: Yellow-Green Group 146B. Anthocyanin: Greyed-Purple Group 183B, present at points of leaflet attachment.

*Margins*.—Entire.

*Prickles*.—A few small prickles underneath.

*Stipitate glands*.—Limited numbers of stipitate glands on margins and underneath.

Hips/seed formation: None observed.

Winter hardiness: Due to its primary use in greenhouse culture, winter hardiness of the variety has not been evaluated.

Disease resistance: Above average resistance to Powdery mildew (*Sphaerotheca pannosa*) and *Botrytis* (*Botrytis cinerea*) diseases under normal growing conditions in Jackson County, Oreg.

I claim:

1. A new and distinct variety of rose plant, as described and illustrated herein.

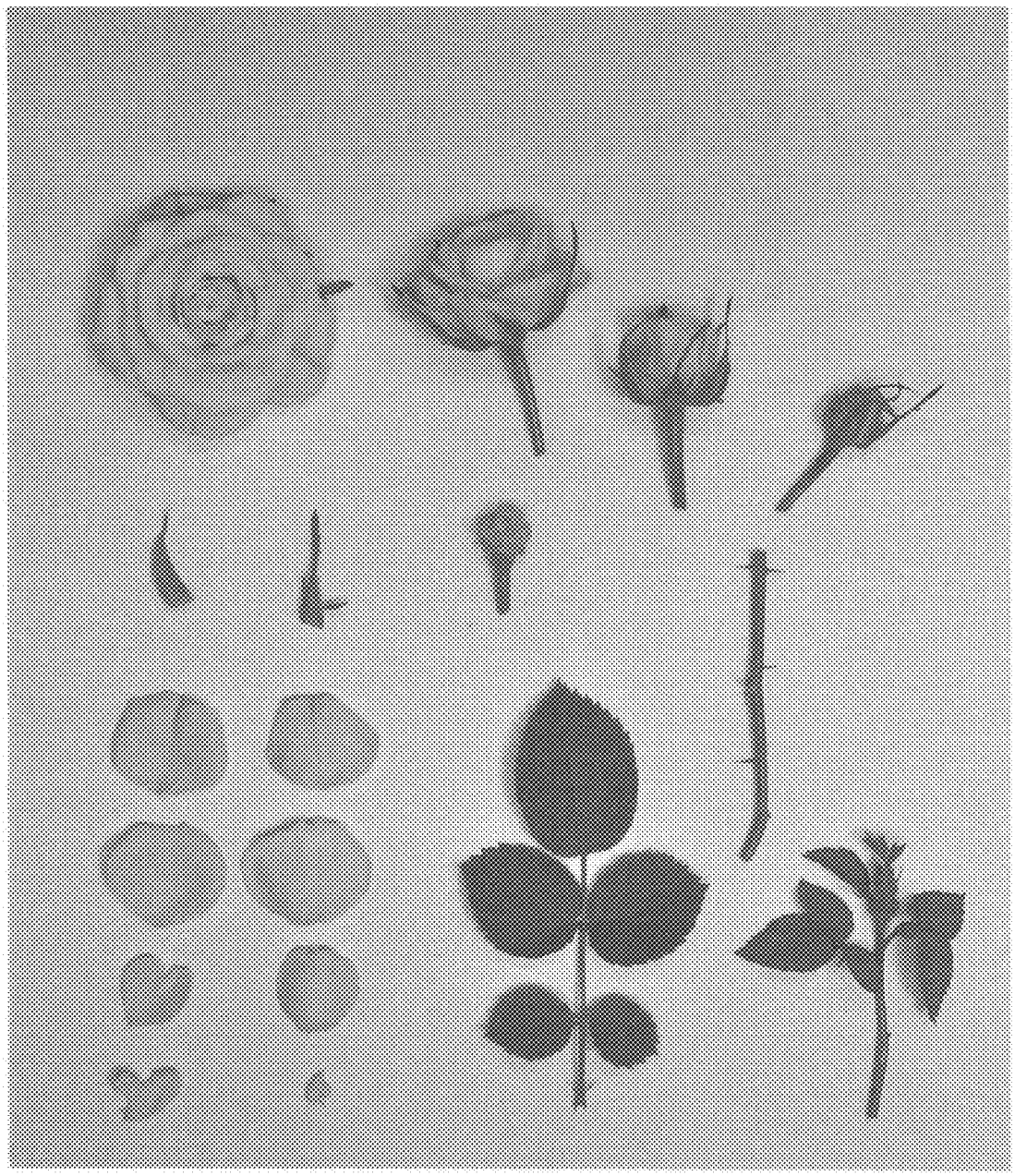

* * * * *